US00PP19444P2

(12) United States Plant Patent
Gragg

(10) Patent No.: US PP19,444 P2
(45) Date of Patent: Nov. 11, 2008

(54) ***AGAVE* PLANT NAMED 'KARA'S STRIPES'**

(50) Latin Name: *Agave attenuata*
Varietal Denomination: KARA'S STRIPES

(76) Inventor: Gary Gragg, 845 Mountain View Dr., Lafayette, CA (US) 94549

( * ) Notice: Subject to any disclaimer, the term of this patent is extended or adjusted under 35 U.S.C. 154(b) by 209 days.

(21) Appl. No.: 11/483,233

(22) Filed: Jul. 7, 2006

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner*—Kent L. Bell
*Assistant Examiner*—Georgia Helmer

(57) ABSTRACT

A new cultivar of *Agave* plant named 'KARA'S STRIPES' that is characterized by clumping habit and variegated foliage that is pale blue-green with broad cream-yellow stripes. In combination these traits set 'KARA'S STRIPES' apart from all other existing varieties of *Agave* known to the inventor.

1 Drawing Sheet

Genus: *Agave.*
Species: *attenuata.*
Denomination: 'KARA'S STRIPES'.

BACKGROUND OF THE INVENTION

The present invention relates to a new and distinct variety of century plant, a perennial succulent grown for use as a container plant. The new cultivar is known botanically as *Agave attenuata* and will be referred to hereinafter by the cultivar name 'KARA'S STRIPES'.

The new *Agave* cultivar named 'KARA'S STRIPES' is a naturally occurring branch sport that was discovered by the inventor on an existing normal colored clump of *Agave attenuata* (species, unpatented) which was growing in the Inventor's garden in Martinez, Calif. in 1999. The parent is an individual *Agave attenuata.* Following initial discovery the inventor isolated, then propagated 'KARA'S STRIPES' growing it on for continuing observation of the dramatic variegation and foliage color. The inventor selected 'KARA'S STRIPES' in 1999 based on the criteria of leaf variegation and leaf color.

*Agave attenuata* 'KARA'S STRIPES' exhibits clumping habit, and semi-translucent strap-like, spineless leaves that radiate outward from the central stalk. The variegated leaves are pale blue-green with broad cream-yellow stripes. With maturity 'KARA'S STRIPES' develops a trunk and offsets, growing in ever expanding clumps, with initial flowering not occurring for sometimes as long as ten years. This variety is grown for its foliage, not for its flower, and no flowers have been observed to date as the plant has not yet reached flowering age.

The dimensions of 'KARA'S STRIPES' after one year are 20 cm. in height and 20 cm. in width. The dimensions of 'KARA STRIPES' at maturity are 120 cm. in height and 90 cm. in width, however when the plant is permitted to offset, the overall clump would eventually become wider than a solitary plant. The new *Agave* variety named 'KARA'S STRIPES' is drought tolerant and hardy to USDA Zones 9 and above. In serious drought the leaves shrivel, however with rain or supplemental water the leaves regain their turgor. Cultural requirements include full sun, well-draining poor to rich well-amended garden soil, and little to regular watering.

The closest comparison plant to 'KARA'S STRIPES' is the parent *Agave attenuata.* Characteristics that distinguish 'KARA'S STRIPES' from the comparison plant are leaf variegation and leaf color. The parent exhibits solid blue-green color leaves, whereas 'KARA'S STRIPES' exhibits variegated leaves that are pale blue-green with broad cream-yellow stripes. Except for leaf variegation and leaf color all other aspects of 'KARA'S STRIPES' are the same as the comparison plant. Other variegated forms of *Agave attenuata* exist, however their white and green color variegation exhibits a harsh visual effect. Those *Agave* experts in the western United States who have seen 'KARA'S STRIPES' attest to the soft and appealing visual effect exhibited by the pale blue-green and cream-yellow coloration of the variegated foliage.

'KARA'S STRIPES' was first asexually propagated in 2001. The first asexual propagation was conducted by the inventor in Lafayette, Calif. and the method used was division of offsets. The characteristics of the new *Agave* cultivar named 'KARA'S STRIPES' are determined fixed, stable and reproduce true to type in successive generations of asexual propagation.

SUMMARY OF THE INVENTION

The following traits have been repeatedly observed and represent the distinguishing characteristics of the new *Agave* variety named 'KARA'S STRIPES'. In combination these traits set 'KARA'S STRIPES' apart from all other *Agave* known to the inventor. 'KARA'S STRIPES' has not been tested under all possible conditions and phenotypic differences may be observed with variations in environmental, climatic and cultural conditions, however, without any variance in genotype.

1. 'KARA'S STRIPES' exhibits clumping habit.
2. 'KARA'S STRIPES' is drought tolerant.
3. 'KARA'S STRIPES' exhibit strap-like spineless leaves.

4. 'KARA'S STRIPES' exhibits dramatic variegated foliage that is pale blue-green with broad cream-yellow stripes.
5. 'KARA'S STRIPES' can grow for as long as ten years before blooming.
6. 'KARA'S STRIPES' is hardy to USDA Zones 9 and above.
7. Cultural requirements for 'KARA'S STRIPES' include full-sun, well-draining poor soil to rich well-amended garden soil, and little to regular watering.
8. 'KARA'S STRIPES' is asexually propagated using the method of division of offsets.

BRIEF DESCRIPTION OF THE DRAWING

The accompanying color drawing labeled

FIG. 1 illustrates plant habit, leaf variegation, and leaf color. The illustrated plant is 2 years old and was transplanted to its current open ground position, in full sun, approximately one year before the photographic drawing was made. The drawing was made using conventional techniques and although color may appear difference from actual color due to light reflectance it is as accurate as possible by conventional photography.

BOTANICAL DESCRIPTION OF THE PLANT

Figure 1:
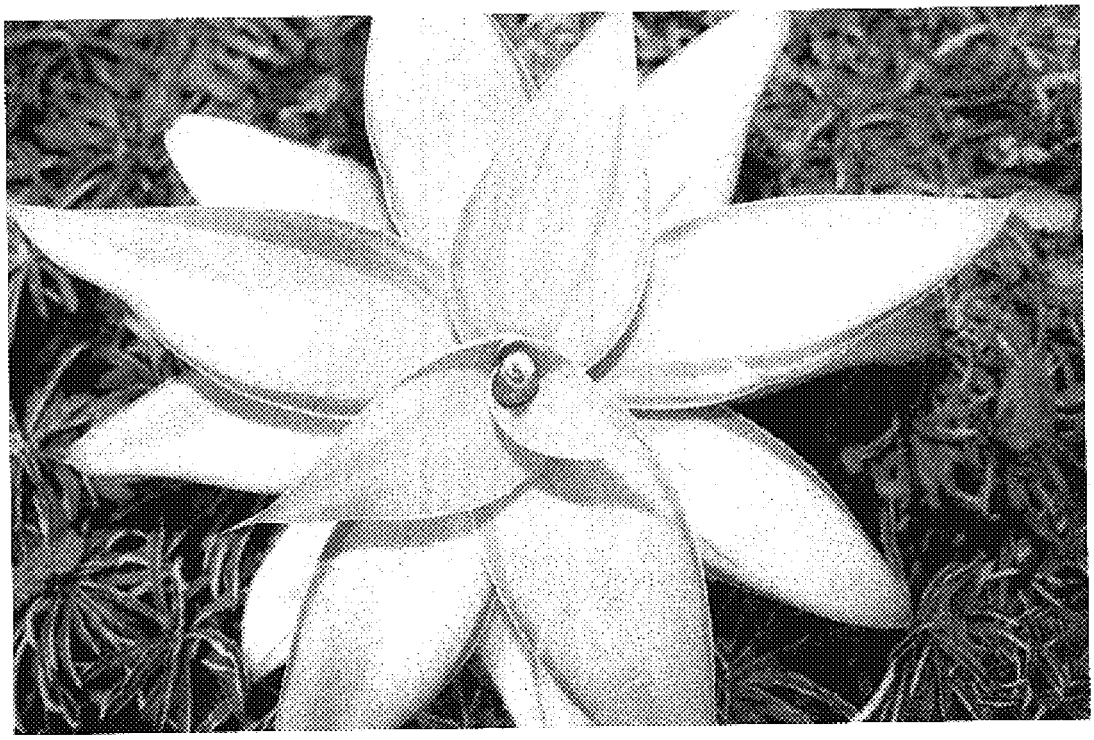
FIG. 1 illustrates the overall appearance of the new *Agave* cultivar named 'KARA'S STRIPES' showing the color as true as it is reasonably possible to obtain in color reproductions of this type. Color in the drawing may differ from the color values cited in the detailed botanical description, which accurately describes the actual color of the new variety 'KARA'S STRIPES'.

The following is a detailed description of the new *Agave* plant named 'KARA'S STRIPES'. Data was collected in Arroyo Grande California in June 2006. The color determinations are in accordance with the 2001 edition of the Royal Horticultural Society Colour Chart, London, England, except where general color terms of ordinary dictionary significance are used. The growing requirements are similar to other *Agave*.

Botanical classification: *Agave attenuata* 'KARA'S STRIPES'.
Family: Agavaceae.
Genus: *AGAVE*.
Species: *attenuata*.
Denomination: 'KARA'S STRIPES'.
Common name: Century plant.
Commercial classification: Perennial succulent.
Plant used: Container plant.
Cultural requirements: Cultural requirements include full-sun, well-draining poor soil to rich well-amended garden soil, and little to regular watering.
Root system: Fibrous.
Plant vigor: Low vigor.
Parentage: *Agave attenuata* 'KARA'S STRIPES' was discovered by the inventor as a naturally occurring branch sport of the following parent:
*Parent plant.*—An individual *Agave attenuata*.
Plant description:
*Bloom time.*—Initial blooming occurs in approximately 10 years.
*Plant habit.*—Clumping.
*Plant dimensions* (*at one year*).—20 cm. in height and 20 cm. in width.
*Plant dimensions* (*at maturity*).—120 cm. in height and 90 cm. in width.
*Plant hardiness.*—USDA Zones 9 and above.
*Asexual propagation.*—Division of offsets.
*Time development roots.*—2 months develop roots on a divided offset.
*Crop time.*—9 to 12 months to produce commercial container plant.
*Disease susceptibility.*—No disease susceptibility known to the inventor.
*Pest susceptibility.*—Mealy bugs can develop at leaf tips.
Foliage:
*Foliage type.*—Evergreen.
*Leaf quantity* (*at one year*).—Average of 15 leaves.
*Dimensions* (*at one year*).—12.5 cm. in length and 6 cm. in width.
*Leaf color* (*adaxial and abaxial surfaces*).—Predominantly cream-yellow 11B, 11C, 11D with yellow-green or grey-green narrow bands along leaf edges, and occasionally within the fully expanded leaves. Bands range in width from 3 mm to 12 mm and consist of colors 190A, 191B, 145B, 145C.
*Shape.*—Ovate to gladiate.
*Division.*—Simple.
*Arrangement.*—Rosette.
*Apex.*—Acuminate.
*Base.*—Truncate.
*Venation.*—Inconspicuous.
*Margins.*—Entire.
*Spines.*—None observed.
*Leaf texture.*—Fleshy.
*Surfaces* (*adaxial and abaxial*).—Glaucous.
*Pubescence.*—None observed.
*Fragrance.*—None observed.
Inflorescence: None observed.
Reproductive organs: None observed.

It is claimed:

1. A new and distinct cultivar of *Agave* plant named 'KARA'S STRIPES' as described and illustrated herein.

* * * * *